US007977388B2

(12) United States Patent
Meier et al.

(10) Patent No.: US 7,977,388 B2
(45) Date of Patent: Jul. 12, 2011

(54) QUINONE DERIVATIVE 2,3-DIMETHOXY-5-METHYL-6-(10-HYDROXYDECYL)-1,4-BENZOQUINONE FOR THE TREATMENT OF MUSCULAR DYSTROPHIES

(75) Inventors: Thomas Meier, Basel (CH); Gunnar Buyse, Herent (BE)

(73) Assignee: Santhera Pharmaceuticals (Schweiz) AG, Liestal (CH)

( * ) Notice: Subject to any disclaimer, the term of this patent is extended or adjusted under 35 U.S.C. 154(b) by 635 days.

(21) Appl. No.: 11/886,388

(22) PCT Filed: Mar. 20, 2006

(86) PCT No.: PCT/EP2006/002536
§ 371 (c)(1),
(2), (4) Date: Nov. 9, 2007

(87) PCT Pub. No.: WO2006/100017
PCT Pub. Date: Sep. 28, 2006

(65) Prior Publication Data
US 2009/0012050 A1    Jan. 8, 2009

(30) Foreign Application Priority Data

Mar. 21, 2005  (EP) ..................................... 05006137

(51) Int. Cl.
*A61K 31/12*     (2006.01)
*A61K 31/56*     (2006.01)
(52) U.S. Cl. ........................................ 514/689; 514/171
(58) Field of Classification Search .................. 514/171, 514/689
See application file for complete search history.

(56) References Cited

U.S. PATENT DOCUMENTS

| 6,133,322 A | 10/2000 | Rustin et al. | |
| 2003/0013772 A1* | 1/2003 | Murphy et al. | 514/674 |
| 2004/0081961 A1* | 4/2004 | Delegeane et al. | 435/6 |

FOREIGN PATENT DOCUMENTS

WO    WO 2006/007910 A1    1/2006

OTHER PUBLICATIONS

McNally, Elizabeth, et al, "Cardiomyopathy in Muscular Dystrophy Workshop Sep. 28-30, 2003, Tuscon, Arizona," Neuromuscular Disorders, vol. 14, pp. 442-448 (2004).*
Silversides, Candice, et al, "Effects of Deflazacort on the Left Ventricular Function in Patients With Duchenne Muscular Dystrophy," The American College of Cardiology, vol. 91, pp. 769-772 (Mar. 2003).*
International Search Report for PCT/EP2006/002536 dated Jul. 20, 2006.
Mealy et al., "Annual Update 2004/2005—Treatment of Neurological Disorders," Drugs of the Future, vol. 30, No. 11, 2005, pp. 1107-1200.
Osako, "The Effects of Idebenone and Glycyrrhizin on *mdx* Mouse Muscle," Journal of the Medical Society of Toho University, vol. 46, No. 1, 1999, pp. 72-80 (English abstract).
Kurihara et al., "Electrical myotonia and cataract in X-linked muscular dystrophy (*mdx*) mouse," Journal of the Neurological Sciences, vol. 99, No. 1, Oct. 1990, pp. 83-92.
English translation of First Office Action (Notice of Reasons for Rejection) received in counterpart Japanese Patent Application No. 2008-502302 dated Feb. 7, 2011 (2 pages).
Ministry of Welfare, the Japanese Government (by trust money on mental/neurological disorder research), article entitled, "Research on the pathology and treatment of muscular dystrophy and related diseases," Takagi Group, Research Report of 1995, Mar. 1996 (in Japanese, with partial English translation) (8 pages).

* cited by examiner

*Primary Examiner* — Raymond J Henley, III
(74) *Attorney, Agent, or Firm* — Kilyk & Bowersox, P.L.L.C.

(57) ABSTRACT

Use of idebenone for the preparation of a medicament for the treating of a muscular dystrophy in particular for treating and/or preventing weakness and/or loss of skeletal muscle tissue and/or cardiomyopathy associated with a muscular dystrophy.

19 Claims, 1 Drawing Sheet

QUINONE DERIVATIVE 2,3-DIMETHOXY-5-METHYL-6-(10-HYDROXYDECYL)-1,4-BENZOQUINONE FOR THE TREATMENT OF MUSCULAR DYSTROPHIES

This application is a National Stage Application of PCT/EP2006/002536, filed Mar. 20, 2006, which claims priority from European Patent Application No. 05006137.3, filed Mar. 21, 2005.

The present invention relates to a method of treating or preventing weakness and loss of skeletal muscle tissue or cardiomyopathy associated with certain forms of muscular dystrophies by using 2,3-dimethoxy-5-methyl-6-(10-hydroxydecyl)-1,4-benzoquinone (idebenone) as the active agent.

BACKGROUND OF THE INVENTION

Duchenne muscular dystrophy (DMD) is a recessively inherited progressive form of muscle-wasting disease affecting ~1 in 3,000 boys. The reported incidence is 25/100,000 live male births worldwide (Katirji, B., Kaminski, H. J., Preston, D. C., Ruff, R. L., Shapiro, B. E. (2002) Neuromuscular disorders in clinical practice. Butterworth Heinemann). First signs of the disease become apparent when boys start to walk. Muscle wasting occurs initially in proximal and later in distal muscle groups leading to the loss of ambulation in teenage patients. Mutations in the dystrophin gene and absence of dystrophin protein ultimately lead to death of DMD patients at early adulthood, mainly because of respiratory or cardiac failures. Clinical measures to improve quality of life comprise orthopedic surgery and nighttime ventilation. Becker muscular dystrophy (BMD) is caused by different mutations of the same dystrophin gene but has a milder clinical course and the patients have a prolonged life expectancy when compared to DMD patients. Cellular processes underlying DMD-associated muscle wasting include the loss of skeletal muscle fibers and accompanying invasion by connective and adipose tissue. Progressive weakness of the skeletal musculature and cardiac involvement leads to early morbidity and mortality in DMD/BMD patients.

Both DMD and BMD are caused by mutations in the dystrophin gene. The dystrophin gene consists of 2700 kbp and is located on the X chromosome (Xp21.2, gene bank accession number: M18533). The 14 kbp long mRNA transcript is expressed predominantly in skeletal, cardiac and smooth muscle and to a limited extent in the brain. The mature dystrophin protein has a molecular weight of ~427 kDa and belongs to the spectrin superfamily of proteins (Brown S. C., Lucy J. A. (eds), "Dystrophin", Cambridge University Press, 1997). While the underlying mutation in DMD leads to a lack of dystrophin protein, the milder BMD-phenotype is a consequence of mutations leading to the expression of abnormal, often truncated, forms of the protein with residual functionality.

X-linked dilated cardiomyopathy (XLDCM) is a progressive and fatal type of heart disease that presents in the second or third decade of life, with congestive heart failure in patients without skeletal muscle weakness (Towbin et al. (1993) X-linked dilated cardiomyopathy; molecular genetic evidence of linkage to the Duchenne muscular dystrophy (dystrophin) gene at Xp21 locus. Circulation 87:1854-65). Different mutations in the dystrophin gene cause selective absence of dystrophin in heart muscle, whereby mutations involving the 5' end of the dystrophin gene result in more severe cardiomyopathy than mutations in the spectrin-like region. With mutations involving the 5' end of the dystrophin gene, the exclusive cardiac involvement seems to be related to a difference in RNA splicing regulation between heart and skeletal muscle. The skeletal muscle maintains dystrophin production by using exon skipping or alternative splicing, whereas the heart muscle is apparently unable to use such mechanisms.

The N-terminal part of dystrophin binds to actin filaments of the cytoskeleton, whereas domains in the C-terminal part of the dystrophin molecule bind to the membrane associated β-dystroglycan. Therefore, dystrophin serves as a molecular linker between the cytoskeleton and the muscle cell membrane and, indirectly, via the so-called dystrophin-associated protein complex (DAPC) also to the extracellular matrix. Known binding partners of dystrophin also include syntrophin, dystrobrevin, the neuronal type nitric oxide synthase (nNOS) and the sarcoglycan-sarcospan (SS) complex. These protein interactions involving both the carboxy- and amino-terminal region of the dystrophin protein are thought to contribute to the mechanical stability of the muscle cell membrane during cycles of contraction and relaxation. Dystrophin is also important for the assembly or integrity of the DAPC-complex itself, as it has been shown that in dystrophin-deficient muscle cells of DMD patients many components of the DAPC complex are reduced or absent in the sarcolemma. Absence of functional dystrophin protein leads to disruption of the mechanical link between actin cytoskeleton and the muscle cell sarcolemma which in turn leads to deterioration of myotubes and muscle weakness (Brown S. C., Lucy J. A. (eds), "Dystrophin", Cambridge University Press, 1997).

Cardiac involvement is present in almost all DMD patients but a clinical manifestation of cardiac and also gastrointestinal defects occurs late in the course of DMD. In a study on incidence and evolution of cardiomyopathy in 328 DMD patients, Nigro et al. (Nigro, G., Comi, L. I., Politano, L. and Bain, R. J. (1990), (Int J Cardiol, 26, 271-277) showed that the incidence of cardiac involvement increased steadily over the teenage years, with approximately one third of the patients being affected by the age of 14, one half of the patients by age 18, and all patients older than 18 years. Dilated cardiomyopathy occurs in 40% of the patients and can be life threatening in later stages of the disease. Previously it has been estimated that 10% to 15% of all DMD patients die from cardiac failure caused by dilated cardiomyopathy (Ishikawa, Y., Bach, J. R. and Minami, R. (1999) Cardioprotection for Duchenne's muscular dystrophy. Am Heart J, 137, 895-902). More recently, with the introduction of ventilatory support to treat respiratory failure, congestive heart failure is becoming one of the major causes of death (currently up to 30% of all DMD patients; Finsterer, J. and Stollberger, C. (2003) The heart in human dystrophinopathies. Cardiology, 99, 1-19).

The cardiac involvement in DMD is characterized by degeneration, atrophy and fibrosis of the myocardium, leading to dilated cardiomyopathy. The process begins in the posterolateral wall of the left ventricle (LV), with septal involvement appearing at later stages. Generally, the right ventricle (RV) is not involved. Early in life (below 12 years), cardiac function is usually interpreted as normal using conventional grey-scale echocardiographic techniques (M-Mode and two-dimensional imaging), which are only capable to detect global abnormalities once the myocardial damage is established. Fractional shortening (FS) and ejection fraction (EF) are the most commonly used parameters to assess LV systolic function, whereas mitral blood flow and pulmonary venous flow are measured to assess diastolic function. It has been shown that DMD patients progressively develop echocardiographic signs of LV dysfunction, which are normally detected around the onset of adolescence (Finsterer, J. and Stollberger, C. (2003) The heart in human dystrophinopathies. Cardiology, 99, 1-19; Sasaki K, et al. (1998) Sequential changes in cardiac structure and function in patients with Duchenne type muscular dystrophy: a two-dimensional echocardiographic study. Am Heart J, 135, 937-944). The first abnormality described is infero-lateral hypokinesia. This is followed by LV dilatation and a reduction in fractional shortening and ejection fraction. Diastolic dysfunction has also been reported in the early stages of the disease (Heymsfield S B, McNish T, Perkins J V, Feiner J M. (1978) Sequence of cardiac changes in Duchenne muscular dystrophy. Am Heart J, 95, 283-294; Kermadec J M, et al. (1994) Prevalence of left ventricular systolic dysfunction in Duchenne muscular dystrophy: an echocardiographic study. Am Heart J, 127, 618-23).

Since the genetic abnormality is present from birth, it can be assumed that ventricular abnormalities in myocardial function are present earlier in life but are not detected using the conventional imaging techniques. Ultrasound tissue characterization, using integrated backscatter, has recently shown evidence for early changes in myocardial ultrastructure prior to development of clinical cardiac involvement (Giglio V, et al. (2003) Ultrasound tissue characterization detects preclinical myocardial structural changes in children affected by Duchenne muscular dystrophy. J Am Coll Cardiol, 24, 309-316). Using Doppler Myocardial velocity Imaging (DMI), a new non-invasive cardiac imaging technique that allows the quantification of regional myocardial function, we have recently shown the presence of regional myocardial dysfunction in young DMD children (aged 3-10 yrs) without cardiac symptoms and with yet normal global cardiac function as assessed by conventional echocardiography (Mertens L, et al. (2004) Early detection of regional myocardial dysfunction in Duchenne muscular dystrophy by ultrasonic strain and strain rate imaging. Neuromusc Disorders, 14: 599-600). With DMI, regional function is assessed by measuring tissue velocities and calculating the cardiac deformation properties regional strain rate and strain (Sutherland G R, et al. (2004) Strain and Strain Rate Imaging: A New Clinical Approach to Quantifying Regional Myocardial Function. *J Am Soc Echocardiogr.* 17:788-802; Weidemann F, Eyskens B, Sutherland G R. (2002) New ultrasound methods to quantify regional myocardial function in children with heart disease. Pediatr Cardiol, 23: 292-306). Compared to normal controls, in young DMD patients we found a significant decrease in radial peak systolic strain rate and strain in the inferolateral (posterior) wall, and in longitudinal peak systolic strain rate and strain in the segments of the LV lateral wall. Recently, it was demonstrated that strain rate is predictive of deterioration in cardiac function and death in children with Duchenne muscular dystrophy, who at the time of the baseline measurement were asymptomatic with normal echocardiographic measures of cardiac function (Giatrokos N. et al.; Strain rate can accurately predict a more aggressive cardiac involvement in asymptomatic patients with Duchenne muscular dystrophy Circulation, November 2004, Supplement).

Pharmacological intervention for the treatment of DMD-associated muscle weakness is currently confined to the use of glucocorticoids such as prednisone or deflazacort. It is well documented that glucocorticoids slow down the loss of muscle mass in DMD patients thus acting as potentially disease-modifying compounds. For example, increased muscle strength has been seen in controlled clinical trials where young DMD patients were treated with glucocorticoids, such as 6α-methylprednisolone-21 sodium succinate (PDN) or deflazacort (Fenichel G M, et al. (1991) Long-term benefit from prednisone therapy in Duchenne muscular dystrophy. Neurology; 41:1874-1877; Reitter B. (1995) Deflazacort vs. prednisone in Duchenne muscular dystrophy: trends of an ongoing study. Brain Dev; 17:39-43; Bonifati M D, et al. (2000) A multicenter, double-blind, randomized trial of deflazacort versus prednisone in Duchenne muscular dystrophy. Muscle Nerve 23:1344-1347). Although trials with daily prednisone or deflazacort have demonstrated increased muscle strength/performance and slowed progression of weakness, as yet there is no universal consensus regarding the use of corticosteroids as standard treatment for DMD. Reasons for this are the lack of sufficient comparative data on the effects of long-term treatment and on the side effects profile in these children. Side effects reported in available clinical trials were weight gain and development of cushinoid facial appearance. However, other side effects have been reported or are major concerns in clinical practice: decreased linear growth, cataracts, osteoporosis and pathological fractures, and behavioral changes. Conclusions of a recent review of available evidence on corticosteroids in DMD were as follows: prednisone (0.75 mg/kg/day) or deflazacort (0.9 mg/kg/day) should be offered as treatment, benefits and side effects should be monitored, and the offer of treatment with corticosteroids should include a balanced discussion of potential risks (Moxley R T, et al. (2005) Practice Parameter Corticosteroid treatment of Duchenne dystrophy. Report of the Quality Standards Subcommittee of the American Academy of Neurology and the Practice Committee of the Child Neurology Society. Neurology 64:13-20). Nevertheless, important questions or issues such as when to start corticosteroid treatment, and fear of significant side effects on the long-term remain. Currently, efforts both in the USA and in Europe are ongoing or being developed to identify which of the many different corticosteroid regimens would be most beneficial with the least of side effects. Few data have been reported suggesting a possible cardioprotective effect of deflazacort (Silversides C K, et al. (2003) Effects of deflazacort on left ventricular function in patients with Duchenne muscular dystrophy. Am J Cardiol 91(6):769-772), but more studies are required as it remains largely unknown whether the use of corticosteroids (targeted to improve skeletal muscle function) could have beneficial or negative effects on the heart in DMD patients.

Dilated cardiomyopathy associated with DMD, BMD and XLMD is currently treated only in advanced stages when symptomatic heart failure becomes apparent or if echocardiographically significant systolic dysfunction is observed that deteriorates progressively. In these circumstances, i.e. at the clinical evident state, clinical practice uses angiotensin converting-enzyme (ACE) inhibitors, beta-blockers or diuretics (Finsterer J., Stöllberger C. (2000) Cardiac involvement in primary myopathies. Cardiology 94:1-11; Bushby K, Muntoni F, Bourke J P. (2003) 107$^{th}$ ENMC international workshop: the management of cardiac involvement in muscular dystrophy and myotonic dystrophy. Neuromusc Disorders 13(2):166-172). These pharmacological interventions are not targeting the cause or specific pathophysiological cellular processes in the cardiomyocytes that underlie the dilated cardiomyopathy associated with DMD/BMD/XLMD. Consequently, their outcome is considered to be limited, and there is a need for the development of new therapeutic interventions specifically targeting the diseased cardiomyocytes in these disorders.

Accordingly, there is a strong need in the art to provide further means for treating and/or preventing several symptoms associated with muscular dystrophies. Said object is achieved by providing idebenone for preparing a medicament for treating and/or preventing weakness and loss of skeletal muscle tissue and/or cardiomyopathies associated with muscular dystrophies.

DESCRIPTION OF THE INVENTION

The present invention relates to a method of treating or preventing weakness and loss of skeletal muscle tissue associated with various forms of muscular dystrophies, in particular Duchenne Muscular Dystrophy (DMD), Becker Muscular Dystrophy (BMD) and Limb Girdle Muscular Dystrophies (LGMDs). Specifically the invention relates to a method to treat muscle weakness in patients suffering from DMD, BMD or LGMD by administering an effective amount of idebenone (2,3-dimethoxy-5-methyl-6-(10-hydroxydecyl)-1,4-benzoquinone).

The invention furthermore relates to a method of treating cardiomyopathies associated with certain forms of muscular dystrophies such as cardiomyopathy associated with Duchenne Muscular Dystrophy (DMD), Becker Muscular Dystrophy (BMD), X-linked dilative cardiomyopathy (XLDCM). Specifically, the invention relates to the administration of idebenone (2,3-dimethoxy-5-methyl-6-(10-hydroxydecyl)-1,4-benzoquinone) to protect DMD, BMD and XLDMC patients from the development of cardiomyopathy, in particular dilated cardiomyopathy or to treat DMD, BMD and XLDMC patients from cardiomyopathy, in particular dilated cardiomyopathy. This is surprising since it has been reported previously that idebenone can be used for the treatment of hypertrophic cardiomyopathy associated with Friedreich's Ataxia (FRDA; U.S. Pat. No. 6,133,322; Rustin et al. (1999) Effect of idebenone on cardiomyopathy in Friedreich's ataxia: a preliminary study. The Lancet, 354: 477-479; Hausse et al. (2002) Idebenone and reduced cardiac hypertrophy in Friedreich's ataxia. Heart 87: 346-349; Buyse et al. (2003) Idebenone treatment in Friedreich's ataxia. Neurological, cardiac, and biochemical monitoring. Neurology 60: 1679-1681). However, hypertrophic cardiomyopathy as seen in FRDA is clinically distinct from dilated cardiomyopathy observed in DMD, BMD and XLDCM-patients.

FRDA patients develop a progressive form of hypertrophic cardiomyopathy related to mitochondrial dysfunction. This is associated with thickening of the myocardial walls with development of predominantly diastolic dysfunction, left ventricular outflow tract obstruction, the risk for ventricular and atrial arrhythmias. In the terminal phase a dilated form of cardiomyopathy has been described in some FRDA patients. In contrast, DMD patients develop a progressive form of dilated cardiomyopathy caused by dystrophin deficiency. In DMD progressive left ventricular systolic dysfunction develops with progressive dilatation of the left ventricle. Often the left ventricular walls become thinner as the ventricle dilates. Ultimately this can lead to clinical overt heart failure and death. Both forms of cardiomyopathy are clinically distinct and therefore it could not have been anticipated by the skilled expert that idebenone can be used to treat dilated cardiomyopathy associated with DMD; BMD and XLMD.

BRIEF DESCRIPTION OF THE DRAWING

Daily running distance (in meters) of wild-type and mdx mice treated with vehicle or with idebenone. The total daily running distance is clearly increased in mdx mice that were treated daily with idebenone indicating the improved endurance capacity and/or muscle strength as well as improved cardiac function.

DETAILED DESCRIPTION OF THE INVENTION

Figure 1:
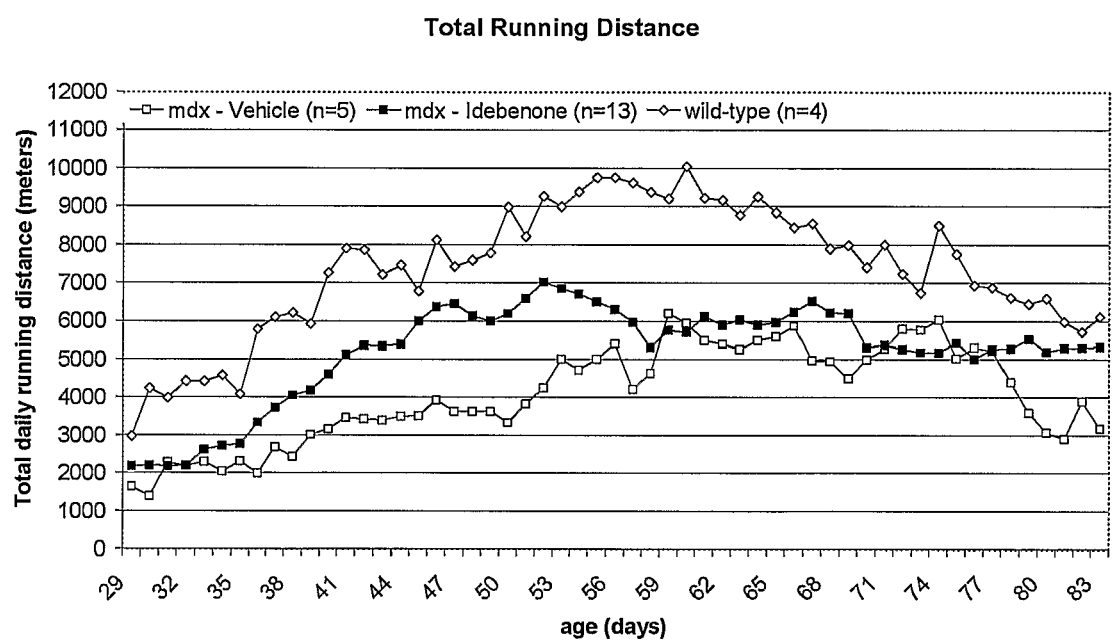

Idebenone is a synthetic analogue of coenzyme Q10 (CoQ10), the vital cell membrane antioxidant and essential constituent of the adenosine-triphosphate (ATP)-producing mitochondrial electron transport chain (ETC). Idebenone has the ability to operate under low oxygen tension situations. Due to its ability to inhibit lipid peroxidation, idebenone protects cell membranes and mitochondria from oxidative damage (Zs.-Nagy I (1990) Chemistry, toxicology, pharmacology and pharmacokinetics of idebenone: a review. Arch. Gerontol. Geriatr. 11:177-186). Its antioxidant properties protect against cerebral ischemia and nerve damage in the central nervous system. Idebenone also interacts with the ETC, preserving ATP formation in ischemic states. This compound is already used as a nootropic drug and has also been shown to stimulate nerve growth factor, a characteristic that could be important in the treatment of Alzheimer's and other neurodegenerative diseases. Idebenone is described in the specification of Japanese Patent Examined Publication No. 3134/1987 filed by Takeda Chemical Industries, Ltd.

Idebenone has the following formula:

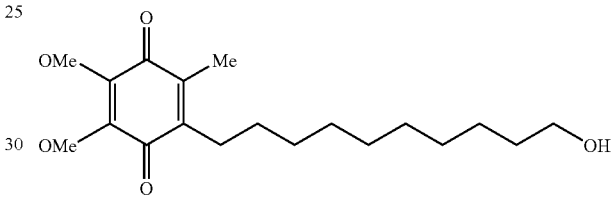

2,3-dimethoxy-5-methyl-6-(10-hydroxydecyl)-1,4-benzoquinone, idebenone

Idebenone is preferably administered in dosage ranges form 5 mg/kg/day to 60 mg/kg/day, more preferably in a dosage range of 5 mg/kg/day to 40 mg/kg/day and most preferred in a dosage range of 10 mg/kg/day to 30 mg/kg/day.

Further, the idebenone is preferably administered at least one, preferably more times a day, preferably for at least 3 months, more preferably for at least 6 months, most preferably for 6 months to 12 months to observe the initial amelioration of muscle force and improved heart function and normalized heart anatomy. For maintenance of the therapeutic effect prolonged treatment is recommended; the preferred treatment is lifelong.

Preferred modes of administration are oral, i.p., i.v., i.m., i.c, parenteral, intranasal and transdermal, whereas the oral administration is the most preferred mode of administration.

Any suitable route of administration may be employed for providing a mammal, especially a human with an effective dosage of idebenone. Further modes of administration include rectal, topical, ocular, pulmonary or nasal administration. The dosage forms include, e.g., tablets, troches, dispersions, suspensions, solutions, capsules, creams, ointments and aerosols, whereas tablets are most preferred.

The effective dosage of the active ingredient employed may vary depending on the particular compounds employed, the mode of administration, the condition being treated and the severity of the condition being treated. Such dosage may be ascertained readily by a person skilled in the art, a preferred dosage having been mentioned above. Idebenone as used in the context of the present invention is preferably formulated into a dosage form prior to administration. Accordingly, the idebenone may be combined with any suitable pharmaceutical carrier. The pharmaceutical preparations for use in accordance with the present invention may be prepared by normal procedures using well-known and readily available ingredients. In making the formulations, idebenone is usually mixed with a carrier, or diluted by a carrier, or enclosed with a carrier, which may be in the form of a capsule, cachet, paper or other container. When the carrier serves as a diluent, it may be a solid, semi-solid, or liquid material, which acts as a vehicle, excipient or medium for the active ingredient. The compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents and/or flavoring agents. The compositions of the invention may be formulated so as to provide quick, sustained or delayed release of the active ingredient after administration to the patient.

Idebenone is toxically safe which means that it can be used as a pharmaceutical active agent in a medicament.

Idebenone can be combined with excipients, fillers, solvents, diluents, dyes and/or binders. The choice of auxiliary substances as well as the amounts thereof to be used depends on whether the medicinal drug is to be administered orally, intravenously, intraperitoneally, intradermally, intramuscularly, intranasally, buccally or topically. For oral application suitable preparations are in the form of tablets, sugar-coated pills, capsules, granular powders, drops, juices and syrups, while for parenteral, topical and inhalative application suitable forms are solutions, suspensions, easily reconstitutable dry preparations as well as sprays. The Idebenone can be administered in a sustained-release substance, in dissolved form or in a plaster, optionally with the addition of agents promoting penetration of the skin, and are suitable as percutaneous application preparations. Forms of preparations that can be used orally or percutaneously may produce a delayed release of the compounds. Idebenone formulations are e.g. described in several patents of Takeda such as for example WO9907355 and JP11116470.

Preferred formulations for use in accordance with the present invention contain 45 mg or 150 mg of Idebenone in a film-coated tablet containing lactose, cellulose, croscarmellose sodium, PVP (Plasdone® K25), magnesium stearate veg. and colloidal silicon dioxide.

In a further preferred embodiment, Idebenone may be administered in combination with a second therapeutic agent, wherein said second therapeutic agent is preferably selected from glucocorticosteroids such as 6a-methylprednisolone-21 sodium succinate (Solumedrol®) or deflazacort (Calcort®) which are routinely used in DMD patients for treatment of inflammation and muscle weakness. Likewise, idebenone may be administered in combination with any medication used in DMD patients to treat DMD-associated cardiomyopathy such as ACE-inhibitors, beta-blockers and diuretics.

In a further preferred embodiment, Idebenone may be administered in combination with a second therapeutic agent, wherein said second therapeutic agent is preferably selected from inhibitors of the cysteine protease calpain or from inhibitors of the proteasome. Preferred calpain inhibitors are those disclosed in WO 2004/078908 A1, WO 2006/021409 A1 and WO 2006/021413 A1.

Idebenone and the further active agent can be used simultaneously, separately or sequentially in order to treat or prevent the disease symptoms. The two active agents may be provided in a single dosage form or a separate formulation, each formulation containing at least one of the two active agents.

The following examples further illustrate the invention.

Example 1

Idebenone improves muscle strength in muscular dystrophy (DMD) patients.

Effect of idebenone on skeletal muscle strength in DMD patients is assessed using a pediatric-focused quantitative muscle testing (QMT) system (CINRG Quantitative Measurement System, CQMS) based upon maximal voluntary isometric contraction. The CINRG QM System has been developed by and used in multiple CINRG (Cooperative International Neuromuscular Research Group) trials in DMD. A study comparing inter-rater reliability of MMT (manual muscle testing) and QMT testing in a group of 12 pediatric muscular dystrophy patients using 12 clinical evaluators from 11 international CINRG clinics, showed that QMT testing is reliable with ICC (inter-rater correlation coefficient)>0.9 for biceps and grip (Escolar et al. (2001); Clinical evaluator reliability for quantitative and manual muscle testing measures of strength in children. Muscle & Nerve 24: 787-793).

Testing is performed by a CQMS trained and experienced clinical evaluator (physical therapist), who participated in the above mentioned CQMS reliability study. Muscles for testing include hand grip (right, left), elbow flexors (right, left), and elbow extensors (right, left). For each muscle group tested, the highest value of two consecutive maximal efforts is recorded. The order of muscle group testing can be maintained throughout the study. In younger, still ambulatory patients additional muscle groups tested by CQMS are knee flexors and knee extensors, and other measures such as timed functional tests (rise from floor, walk/run 10 meters, climb four stairs) are included as well.

Pulmonary function testing includes forced vital capacity (FVC) and negative inspiratory force (NIF). Measurements can be done using the CINRG Quantitative Measurement System (CQMS).

The above described testing allows the monitoring of any muscle strength improvement as the result of the idebenone treatment.

Example 2

Idebenone improves dilated cardiomyopathy in muscular dystrophy (DMD) patients.

Therapeutic effect of idebenone on the dilated cardiomyopathy can be detected by 2D and M-mode echocardiography and by tissue color Doppler methodology to quantify regional myocardial function (Weidemann F, Eyskens B, Sutherland G R. (2002) New ultrasound methods to quantify regional myocardial function in children with heart disease. Pediatr Cardiol, 23: 292-306). Specifically, real time 2-dimensional Color Doppler Myocardial Imaging (CDMI) data were recorded using GE Vingmed System V (Horten, Norway; 3.5 MHz) to evaluate longitudinal function from the interventricular septum, the LV lateral wall and the RV free wall using the standard apical 4-chamber view. To evaluate radial function in the LV infero-lateral wall, CDMI data are recorded from the parasternal short axis view. All data are acquired at a high frame rates of 120-250 frames/s using the narrowest image sector angle possible (usually 30°) and the optimal depth of imaging to increase temporal resolution. Aliasing is eliminated from the CDMI data sets by setting appropriate pulse repetition frequency values (range 14 to 28 cm/sec). For longitudinal views, care must be taken to keep each wall in the center of the ultrasound sector in an attempt to align the ultrasonic beam as near zero degrees as possible with longitudinal motion. Three cardiac cycles are stored in a cineloop format for subsequent post-processing.

All data are digitally transferred from the ultrasound machine and post-processed on an off-line workstation. The CDMI data sets are analyzed using dedicated software (Software Package For Echocardiographic Quantification Leuven, Speqle 4©, Catholic University of Leuven, Belgium). This allows the computation of regional myocardial velocities, natural SR and ε values.

In each segment peak systolic and peak early diastolic (E') and late diastolic (A) myocardial velocities are measured. The ratio of the early mitral diastolic blood flow over the early diastolic septal myocardial velocity (E/E') is measured as an indicator of diastolic function.

Appropriate software (e.g. Speqle4) is used to calculate strain rate (SR) and strain (ε) in the different myocardial segments. SR measures the rate of deformation of a myocardial segment and corresponds to the local spatial velocity gradient (Sutherland G R, et al. (2004) Strain and Strain Rate Imaging: A New Clinical Approach to Quantifying Regional Myocardial Function. J Am Soc Echocardiogr, 17: 788-802). It is expressed in sec-1. For the longitudinal direction, when the segment shortens (systole), it gives a negative SR value. When the segment lengthens (diastole), it is characterized by a positive value. ε defines the amount of local deformation in terms of percentage and is derived by time integrating the mean SR values. Myocardial longitudinal ε values describe regional shortening in systole and are expressed with a negative value. In contrast, both ε and SR in the radial direction are expressed as positive values. Longitudinal peak systolic SR and ε are estimated for the basal, mid, and apical segments of each wall by measuring the spatial velocity gradient over a computation area of 10 mm. A computation area of 5 mm is used for the radial SR estimation. A manual M-mode based tracking algorithm is applied to maintain the sample volume within the region of interest throughout the cardiac cycle. To determine the duration of ejection, the aortic valve opening and closure clicks are introduced and aligned from blood pool pulsed wave Doppler tracings recorded from cycles with a comparable R-R interval.

The Isovolumetric Velocity Acceleration (IVA) is measured according to the description by M. Vogel (Vogel M et al. (2002) Validation of myocardial acceleration during isovolumetric contraction as a novel noninvasive index of right ventricular contractility: comparison with ventricular pressure-volume relations in an animal model. Circulation 105(14): 1693-1699). The sample volume is placed in the middle of the myocardium at the basal free wall. Isovolumetric velocity acceleration is calculated as the difference between baseline and peak velocity divided by their time interval. Measurements of myocardial acceleration and velocities are calculated from 3 consecutive cardiac cycles with the average of the 3 measurements recorded.

The above testing allows the monitoring of any improvement of dilated cardomyopathy as the result of the idebenone treatment.

Example 3

Study Hypothesis

Without being bound to any theory by reducing oxidative stress and improving mitochondrial respiratory chain function, idebenone therapy improves the cardiomyopathy associated with dystrophin deficiency in DMD patients and improves skeletal muscle strength/performance.

Parameters of the Treatment—inclusion: Duchenne muscular dystrophy (DMD) patients, male, age 10-16 yrs
duration: 12 months, with assessments at baseline, 6 months, and 12 months.
primary endpoint: cardiac function
secondary endpoints: skeletal muscle strength, respiratory function, biochemical cardiac markers
treatment regimen: idebenone, oral, fixed dose, using 150 mg tablets, 3×150 mg/day;

Patient Selection:

Patients age 10-16 years with confirmed diagnosis for DMD by a positive test for dystrophin gene deletion, dystrophin gene point mutation or dystrophin protein deficiency on biopsy with a clinical picture consistent of typical DMD are included in the study. Patients on chronic glucocorticosteriod treatment (e.g. prednisone, deflazacort) are included only if corticosteroids dosage has been stable for at least 6 months prior to the administration of idebenone. Likewise, patients on chronic medication for DMD associated cardiomyopathy (ACE-inhibitors, beta-blockers and/or diuretics) are included only if dosage of these medications has been stable for at least 3 months prior to administration of idebenone.

Treatment Protocol:

Patients receive idebenone as 150 mg tablets with a dosage regimen of 1×150 mg tablet three times a day (morning, midday and evening) to be taken during or directly after a meal (resulting in 7.5-18 mg/kg/d for the estimated body weight range of 25-60 kg). Treatment duration is 12 months with assessment of endpoints after 6 and 12 months.

Study Endpoints:
A) Cardiac endpoints met when:
significantly different from placebo in peak systolic radial strain of the left ventricular (LV) posterior (inferolateral) wall (primary endpoint)
significantly different from placebo in peak systolic radial strain rate LV posterior (inferolateral) wall
significantly different from placebo in peak systolic longitudinal strain and strain rate LV wall (lateral wall, interventricular septum)
significantly different from placebo in global left ventricular function such as fractional shortening or ejection fraction
significantly different from placebo in left ventricular diastolic function such as for example pulmonary venous flow, mitral inflow, tissue doppler velocities
significantly different from placebo in isovolumetric acceleration (IVA) in the left ventricular basal segment
significantly different from placebo in heart rate
B) Neurological endpoints are met when:
significantly different from placebo in muscle strength (measured in pounds) using the CINRG Quantitative Measurement System (CQMS) which includes measures of hand grip strength (right, left), upper limb QMT score (sum of elbow flexion and elbow extension, right and left) whereby for each measurement the best of 2 consecutive attempts is recorded significantly different from placebo in timed functional test for ambulant patients: time to walk 10 meters (measured in seconds)

significantly different from placebo in pulmonary function testing (PFTs) using CQMS measuring FVC (forced vital capacity; in % predicted) or NIF (negative inspiratory force measured in measured in $cmH_2O$).

Statistical Power Calculation:

With a total sample size of 21 subjects allocated with a 2:1 ratio to Idebenone and Placebo a difference of 15% in peak systolic strain (%) as primary endpoint between the groups can be detected with a power of 80% and a one-sided significance level of 5%. The power calculation assumes a standard deviation of 12% for both groups.

Methods for Detecting the Therapeutic Effect of Idebenone Treatment:

1. Cardiac:
a. Standard echocardiographic examination including:
  1. Standard echocardiographic windows with gray-scale and color Doppler imaging: standard apical four-chamber view, long-axis view, short axis views (papillary muscle level, level aortic valve and RVOT), RVOT view, subcostal view on RVOT
  2. M-mode in short axis at level of papillary muscles measuring left ventricular end-systolic dimension, left ventricular end-diastolic dimension, shortening fraction, ejection fraction, right ventricular end diastolic dimension, right ventricular end systolic dimension.
  3. Calculation of LV ejection fraction using the standard modified Simpson's formula: cineloops of the apical four chamber view and two chamber view must be stored (3 consecutive cardiac cycles)
  4. Mitral inflow pattern: Three consecutive pulsed Doppler traces at the level of the tips of the mitral leaflets must be stored. E-velocity, A-velocity, E/A ratio, deceleration time, A-duration and IVRT are measured.
  5. Pulmonary venous flow: Three consecutive pulsed-Doppler traces about 1 cm in the right upper pulmonary vein must be stored. Systolic velocity, diastolic velocity, A-wave reversal velocity and A-wave reversal duration are measured.
  6. Tricuspid inflow: Three consecutive pulsed Doppler traces at the level of the tips of the tricuspid leaflets must be stored. E-velocity, A-velocity, E/A ratio, deceleration time, A-duration are measured.
  7. LVOT diameter are measured in the long axis view.
  8. Pulsed Doppler of LVOT: three consecutive pulsed Doppler traces are measured in LVOT below level of aortic valve. Vmax and velocity time integral (VTI) are measured. Together with measurement of LVOT diameter, this is used to calculate cardiac output.
  9. CW Doppler across aortic valve: three consecutive pulsed Doppler traces are measured across the aortic valve. Vmax and VTI are measured.
  10. Tricuspid regurgitation: three consecutive CW Doppler traces of the tricuspid regurgitation signal are stored if it can be acquired. Maximal velocity is assessed.
  11. RVOT flow: three consecutive CW Doppler traces are measured across the RVOT. Vmax is measured. Six pulsed wave Doppler measurements are performed at the level of the pulmonary valve. Vmax is measured. Aortic valve and mitral valve regurgitation: this is assessed using color flow imaging.
b. Color Doppler Myocardial Imaging (CDMI):
  Tissue color Doppler methodology is used to quantify regional myocardial function (Weidemann et al, 2002, Pediatr Cardiol 23: 292-306). Real time 2-dimensional Color Doppler Myocardial Imaging (CDMI) data is recorded to evaluate longitudinal function from the interventricular septum, the LV lateral wall and the RV free wall using the standard apical 4-chamber view. To evaluate radial function in the LV inferolateral wall, CDMI data are recorded from the parasternal short axis view. All data are acquired at a high frame rates of 120-250 frames/s using the narrowest image sector angle possible (usually 30°) and the optimal depth of imaging to increase temporal resolution. Aliasing is eliminated from the CDMI data sets by setting appropriate pulse repetition frequency values (range 14 to 28 cm/sec). For longitudinal views, care is taken to keep each wall in the center of the ultrasound sector in an attempt to align the ultrasonic beam as near zero degrees as possible with longitudinal motion. Three cardiac cycles are stored in a cineloop format for subsequent post-processing.

c. CDMI Data Analysis:

All data are digitally transferred from the ultrasound machine and post-processed on an off-line workstation. The CDMI data sets are analyzed using dedicated software (Software Package For Echocardiographic Quantification Leuven, Speqle 4©, Catholic University of Leuven, Belgium). This allows the computation of regional myocardial velocities, natural SR and $\epsilon$ values.

In each segment peak systolic and peak early diastolic (E') and late diastolic (A') myocardial velocities are measured. The ratio of the early mitral diastolic blood flow over the early diastolic septal myocardial velocity (E/E') is measured as an indicator of diastolic function.

Speqle4 software is used to calculate strain rate (SR) and strain in the different myocardial segments. SR measures the rate of deformation of a myocardial segment and corresponds to the local spatial velocity gradient. It is expressed in sec-1. For the longitudinal direction, when the segment shortens (systole), it gives a negative SR value. When the segment lengthens (diastole), it is characterized by a positive value. $\epsilon$ defines the amount of local deformation in terms of percentage and is derived by time integrating the mean SR values. Myocardial longitudinal $\epsilon$ values describe regional shortening in systole and are expressed with a negative value. In contrast, both $\epsilon$ and SR in the radial direction are expressed as positive values. Longitudinal peak systolic SR and $\epsilon$ is estimated for the basal, mid, and apical segments of each wall by measuring the spatial velocity gradient over a computation area of 10 mm. A computation area of 5 mm is used for the radial SR estimation. A manual M-mode based tracking algorithm is applied to maintain the sample volume within the region of interest throughout the cardiac cycle. To determine the duration of ejection, the aortic valve opening and closure clicks are introduced and aligned from blood pool pulsed wave Doppler tracings recorded from cycles with a comparable R-R interval.

The Isovolumetric Velocity Acceleration (IVA) is measured according to the description by M. Vogel. The sample volume is placed in the middle of the myocardium at the basal free wall. Isovolumetric velocity acceleration is calculated as the difference between baseline and peak velocity divided by their time interval. Measurements of myocardial acceleration and velocities are calculated from 3 consecutive cardiac cycles with the average of the 3 measurements recorded.

2. Skeletal Muscle Strength & Respiratory Function:

Skeletal muscle strength is assessed using a pediatric-focused quantitative muscle testing (QMT) system (CINRG Quantitative Measurement System, CQMS) based upon maximal voluntary isometric contraction. The CINRG QM System has been developed by and used in multiple CINRG (Cooperative International Neuromuscular Research Group) trials in DMD (Escolar et al, 2001, Muscle & Nerve 24: 787-793).

Testing is performed by a CQMS trained and experienced clinical evaluator (physical therapist), who participated in the above mentioned CQMS reliability study. Muscles tested includes hand grip (right, left), elbow flexors (right, left), and elbow extensors (right, left). For each muscle group tested, the highest value of two consecutive maximal efforts is recorded. The order of muscle group testing is maintained throughout the study.

Pulmonary function testing includes forced vital capacity (FVC) and negative inspiratory force (NIF). Measurements are done using the CINRG Quantitative Measurement System (CQMS).

Example 4

Animal Model of DMD

More than twenty years ago, the X chromosome-linked muscular dystrophy (mdx) mutation was identified in mice (Bulfield G, Siler W G, Wight P A L, Moore K J (1984); X chromosome-linked muscular dystrophy (mdx) in the mouse; Proc Natl Acad Sci USA. 81:1189-1192). Since then this mdx mouse has become a widely used animal model for Duchenne muscular dystrophy (DMD). This is justified since several of the key pathological manifestations of dystrophin-deficiency seen in DMD patients are also observed in the mdx mouse model. For example, like in human DMD patients, lack of dystrophin leads to muscle cell membrane instability in muscle tissue of the mdx mouse. Disintegrated cell membranes in turn lead to the unregulated influx of calcium resulting in impaired calcium homeostasis (Bradley W G, Fulthorpe J J (1978); Studies of sarcolemmal integrity in myopathic muscle. Neurology 28: 670-677). Mitochondria are considered a prominent site of calcium-mediated cellular toxicity (Robert V, Massimino M L, Tosello V, Marsault R, Cantini M, Sorrentino V, Poznan T (2001). Alteration in calcium handling at the subcellular level in mdx myotubes. J Bid Chem 276: 4647-4651) linking dystrophin-deficiency to mitochondrial dysfunction and also oxidative stress (Kuznetsov et al. (1998) Impaired mitochondrial oxidative phosphorylation in skeletal muscle of the dystrophin-deficient mdx mouse. Mol Cell Biochem. 183: 87-96; Robert V et al. (2001) Alteration in calcium handling at the subcellular level in mdx myotubes. J. Biol. Chem. 276: 4647-51; Rodriguez M C, Tarnopolsky M A (2003) Patients with dystrophinopathy show evidence of increased oxidative stress. Free Radic. Biol. Med. 34: 1217-20; Nakae et al. (2004). Early onset of lipofuscin accumulation in dystrophin-deficient skeletal muscle of DMD patients and mdx mice. J. Mol. Histol. 35: 489-99).

Mdx mice like DMD patients develop dilated cardiomyopathy with evidence of cardiomyocyte hypertrophy and necrosis as well as cardiac fibrosis (Quinlan J G, Hahn H S, Wong B L, Lorenz J N, Wenisch A S, Levin L S (2004). Evolution of the mdx mouse cardiomyopathy: physiological and morphological findings. Neuromuscul Disord 14: 491-496). Furthermore, the marked pathological changes in mdx mouse muscle include necrosis followed by fibrosis and macrophage infiltration (Stedman H H, Sweeney H L, Shrager J B, Maguire H C, Panettieri R A, Petrof B, Narusawa M, Leferovich J M, Sladky J Z, Kelly A M (1991) Nature 352: 536-539). As a consequence of this cellular pathology mdx mice show reduced muscle strength. This can be demonstrated functionally using various exercise parameters which are generally impaired in dystrophic mdx mice as compared to healthy wild type mice. The analysis of mdx mice in a voluntary wheel running setup, for example, showed that mdx mice run less than wild type control mice and that they have an abnormal running endurance (Hara H, Nolan P M (2002). Running endurance abnormality in mdx mice. Muscle Nerve 25: 207-11). Thus, mdx mice are a well recognized and widely used model for the analysis of the effect of new drugs on the performance/physiology in dystrophic mice (Granchelli et al. (2000) Pre-clinical screening of drugs using the mdx mouse. Neuromuscul. Disord. 10:235-239).

The effect of idebenone on the running performance was tested in the dystrophin-deficient mdx mouse, a validated animal model for DMD. Starting at day 21 of age, mdx mice were treated with idebenone. Their daily running performance was compared to mdx mice treated with vehicle only and to non-treated wild-type mice. For this, idebenone was dissolved in 0.5% w/v carboxymethylcellulose (CMC) to a final concentration of 20 mg/ml. Idebenone (20 mg/ml in 0.5% CMC) was applied once a day by gavage feeding. The final dose of idebenone at all time points was 200 mg/kg body weight. Control mice received the same amount of vehicle only.

Surprisingly, it was found that idebenone treatment leads to a prominent increase in the daily running performance in mdx mice. As demonstrated in FIG. 1, vehicle-treated mdx mice run much less compared to wild-type mice over the entire time period analyzed (29-84 days of age). Idebenone treated mdx mice performed clearly better compared to the vehicle-treated mdx mice from the start of the analysis.

Non-exercised mdx develop a heart phenotype only relatively late (Quinlan J G, Hahn H S, Wong B L, Lorenz J N, Wenisch A S, Levin L S (2004). Evolution of the mdx mouse cardiomyopathy: physiological and morphological findings. Neuromuscul Disord 14: 491-496), while exercise accelerates the development of a heart phenotype in mdx mice (Nakamura A, Yoshida K (2002). Progression of dystrophic features and activation of mitogen-activated protein kinases and calcineurin by physical exercise, in hearts of mdx mice. FEBS Lett 520: 18-24). Furthermore, cardiomyocytes from mdx mice are abnormally vulnerable to mechanical stress-induced injury, thereby resulting in a loss of sarcolemmal integrity and contractile dysfunction (Danialou G, Comtois A S (2001). Dystrophin-deficient cardiomyocytes are abnormally vulnerable to mechanical stress-induced contractile failure and injury. Faseb J 15: 1655-1657). Idebenone's well established antioxidant properties as well as its capacity to facilitate electron flux in functionally impaired mitochondria are the most likely explanations for the molecule's cell protecting effect. Specifically, idebenone may protect cardiomyocytes in the mdx mouse in a comparable manner as it has been shown in a mouse model for Friedreich Ataxia (Seznec H, Simon D (2004). Idebenone delays the onset of cardiac functional alteration without correction of Fe—S enzymes deficit in a mouse model for Friedreich ataxia. Hum Mol Genet 13: 1017-1024).

The invention claimed is:

1. A method for treating a muscular dystrophy, that includes treating weakness and/or loss of skeletal muscle tissue and/or cardiomyopathy associated with a muscular dystrophy, said method comprising administering an effective amount of a medicament comprising idebenone to a patient in need of such treatment.

2. The method according to claim 1, wherein the weakness and/or loss of skeletal muscle tissue is associated with Duchenne Muscular Dystrophy (DMD), Becker Muscular Dystrophy (BMD) and/or Limb Girdle Muscular Dystrophies (LGMD).

3. The method according to claim 1, wherein the cardiomyopathy is associated with Duchenne Muscular Dystrophy (DMD), Becker Muscular Dystrophy (BMD), X-linked Dilative Cardiomyopathy (XLDCM) and/or Limb Girdle Muscular Dystrophies (LGMD).

4. The method according to claim 1, wherein the cardiomyopathy is dilated cardiomyopathy.

5. The method according to claim 1, wherein the idebenone is administered in a dosage of from 5 mg/kg/day to 60 mg/kg/day.

6. The method according to claim 1, wherein the idebenone is administered one or more times daily over at least 3 months.

7. The method according to claim 1, wherein the mode of administration of idebenone is oral, i.p., i.v., i.m., i.c., parenteral, intranasal or transdermal.

8. The method according to claim 1, wherein the idebenone is orally administered.

9. The method according to claim 1, wherein the idebenone is administered in a form of a tablet.

10. The method according to claim 1, wherein the idebenone is administered in combination with a second therapeutic agent.

11. The method according to claim 10 wherein the second therapeutic agent is a glucocorticosteroid or a medication for the treatment of DMD-associated cardiomyopathy.

12. The method according to claim 10 wherein the second therapeutic agent is selected from inhibitors of the cysteine protease calpain or inhibitors of the proteasome complex.

13. The method of claim 11, wherein said second therapeutic agent is 6α-methylprednisolone-21 sodium succinate or deflazacort.

14. The method of claim 11, wherein said second therapeutic agent is an ACE-inhibitor, a beta-blocker, and/or a diuretic.

15. The method according to claim 1, wherein the idebenone is administered one or more times daily over a lifetime.

16. The method according to claim 1, wherein the idebenone is administered in a dosage of from 10 mg/kg/day to 30 mg/kg/day.

17. The method according to claim 1, wherein the idebenone is administered in a dosage of from 5 mg/kg/day to 40 mg/kg/day.

18. The method according to claim 1, wherein the idebenone is administered one or more times daily for about 6 to about 12 months.

19. The method according to claim 1, wherein the idebenone is administered one or more times daily over at least 6 months.

* * * * *